United States Patent
Graziani

(10) Patent No.: US 11,369,325 B2
(45) Date of Patent: Jun. 28, 2022

(54) ADVANCED CONCEPT MOBILE X-RAY IMAGING DEVICE

(71) Applicant: General Electric Company, Schenectady, NY (US)

(72) Inventor: Stephane Graziani, Buc (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1025 days.

(21) Appl. No.: 15/420,344

(22) Filed: Jan. 31, 2017

(65) Prior Publication Data

US 2018/0214112 A1   Aug. 2, 2018

(51) Int. Cl.
*A61B 6/00* (2006.01)

(52) U.S. Cl.
CPC .......... *A61B 6/4405* (2013.01); *A61B 6/4283* (2013.01); *A61B 6/4411* (2013.01); *A61B 6/4458* (2013.01); *A61B 6/464* (2013.01); *A61B 6/587* (2013.01)

(58) Field of Classification Search
CPC .... A61B 6/08; A61B 6/40; A61B 6/42; A61B 6/44; A61B 6/4429; A61B 6/4452; A61B 6/4458; A61B 6/4476; A61B 6/4482; A61B 6/54; A61B 6/545; A61B 6/547; A61B 6/58; A61B 6/587; A61B 6/588; A61B 34/00; A61B 34/20; A61B 34/25; A61B 34/30; A61B 34/32; A61B 34/35; A61B 2034/305; A61B 2034/2046; A61B 2034/2055; A61B 2034/2057; A61B 2560/00; A61B 2560/02; A61B 2560/0223; A61B 2560/0228; A61B 2560/0233; A61B 2560/0266; A61B 2560/0271; A61B 2560/04; A61B 2560/0406; A61B 2560/0431; A61B 2560/0437; A61B 2560/0443; A61B 2560/045; A61B 2560/0456; A61B 2560/0462; A61B 2560/0487; A61N 5/1048; A61N 5/1049; A61N 5/1077; A61N 5/1083; A61N 2005/105; A61N 2005/1051; H01J 2237/02; H01J 2237/15; H01J 2237/1502; H01J 2237/248; H01J 2237/2482

See application file for complete search history.

(56) References Cited

U.S. PATENT DOCUMENTS

| | | | |
|---|---|---|---|
| 2010/0324380 A1* | 12/2010 | Perkins | A61B 5/0002 600/301 |
| 2011/0317816 A1* | 12/2011 | Bechard | A61B 6/00 378/98.8 |
| 2012/0148031 A1* | 6/2012 | Eaves | A61B 6/4405 378/198 |
| 2013/0003939 A1* | 1/2013 | Bouvier | A61B 6/4405 378/198 |
| 2015/0049862 A1* | 2/2015 | Ancar | A61B 6/08 378/190 |

* cited by examiner

*Primary Examiner* — Anastasia Midkiff
(74) *Attorney, Agent, or Firm* — Fletcher Yoder, P.C.

(57) ABSTRACT

A mobile X-ray system includes a movable base, a robotic arm mounted on the movable base, an X-ray source attached to the robotic arm, a radiation detector, one or more user interfaces, and a controller configured to determine a position of the X-ray source and a position of the detector and to automatically move the base and the robotic arm to align the X-ray source with the detector.

19 Claims, 14 Drawing Sheets

ADVANCED CONCEPT MOBILE X-RAY IMAGING DEVICE

FIELD

The disclosed exemplary embodiments relate generally to X-ray systems, and more particularly to mobile X-ray imaging systems.

BACKGROUND

A number of X-ray imaging systems of various designs are known and are presently in use. Such systems are generally based upon generation of X-rays that are directed toward a subject of interest. The X-rays traverse the subject and impinge on a detector, for example, a film, an imaging plate, or a portable cassette. The detector detects the X-rays, which are attenuated, scattered or absorbed by the intervening structures of the subject. In medical imaging contexts, for example, such systems may be used to visualize the internal structures, tissues and organs of a subject for the purpose screening or diagnosing ailments. X-ray systems may be fixed or mobile. Mobile radiation systems generally utilize an X-ray source mounted on a movable platform. However, present mobile X-ray systems may have a relatively large footprint, may be difficult to move and manipulate into position, and may be difficult to align for imaging. Furthermore, present mobile X-ray systems may be bulky and may be difficult to see around, in particular when moving, and may have permanently installed controls that limit maneuverability and operability from different user positions. It would be advantageous to provide a mobile X-ray system that overcomes these and other disadvantages.

SUMMARY

The disclosed embodiments are directed to a mobile X-ray system including a movable base, a robotic arm mounted on the movable base, an X-ray source attached to the robotic arm, a radiation detector, one or more user interfaces, and a controller configured to determine a position of the X-ray source and a position of the detector and to automatically move the base and the robotic arm to align the X-ray source with the detector.

The movable base may include one or more drive wheels and a drive system configured to provide power to the one or more drive wheels.

The drive system may be configured to provide steering forces in a horizontal plane and motive forces in a vertical plane to the one or more drive wheels.

The drive system may be configured to provide the steering forces and motive forces to the one or more drive wheels to cause the mobile X-ray system to rotate around a vertical axis.

The robotic arm may include a plurality of joints and arm members providing multiple degrees of freedom.

The mobile X-ray system may also include one or more first sensors mounted on the X-ray source and one or more second sensors mounted on the detector. The first and second sensors may be connected to the controller, and the controller may be configured to determine the position of the X-ray source and the detector from signals produced by the first and second sensors.

The first sensors may be distance sensors configured to measure a distance to the second sensors and transmit the distance information to the controller, and the controller may be configured to determine the position of the X-ray source and the detector from the distance information.

The first and second sensors may be three dimensional position sensors configured to transmit three dimensional position information to the controller, and the controller may be configured to determine the position of the X-ray source and the detector from the three dimensional position information.

The one or more user interfaces may include a first display screen and a camera mounted on opposite sides of the mobile X-ray system, wherein images collected by the camera are transmitted to the first user interface to provide a view of an area in front of the mobile X-ray system opposite the first display screen.

The one or more user interfaces may also include a second detachable display screen for controlling movement and image acquisition of the mobile X-ray system.

The disclosed embodiments are also directed to a method of operating a mobile X-ray system including using a sensor system to determine a position of an X-ray source and a position of a radiation detector of the mobile X-ray system, and using a controller to automatically move a movable base and a robotic arm of the mobile X-ray system to align the X-ray source with the detector based on signals from the sensor system.

The method may include using the controller to operate a drive system of the mobile X-ray system to provide power to one or more drive wheels to move the movable base.

The controller may be used to operate the drive system to provide steering forces in a horizontal plane and motive forces in a vertical plane to the one or more drive wheels to move the movable base.

The controller may also be used to operate the drive system to provide the steering forces and motive forces to the one or more drive wheels to cause the mobile X-ray system to rotate around a vertical axis.

The sensor system may include one or more first sensors mounted on the X-ray source and one or more second sensors mounted on the detector, and the method may include using the controller to determine the position of the X-ray source and the detector from signals produced by the first and second sensors.

The method may further include using the first sensors to measure a distance to the second sensors and transmit the distance information to the controller and using the controller to determine the position of the X-ray source and the detector from the distance information.

The first and second sensors may be used to transmit three dimensional position information to the controller and the controller may be used to determine the position of the X-ray source and the detector from the three dimensional position information.

A first display screen and a camera mounted on opposite sides of the mobile X-ray system may be used to provide a view of an area in front of the mobile X-ray system opposite the first display screen.

A second detachable display screen may be used for controlling movement and image acquisition of the mobile X-ray system.

DETAILED DESCRIPTION

Figure 1:
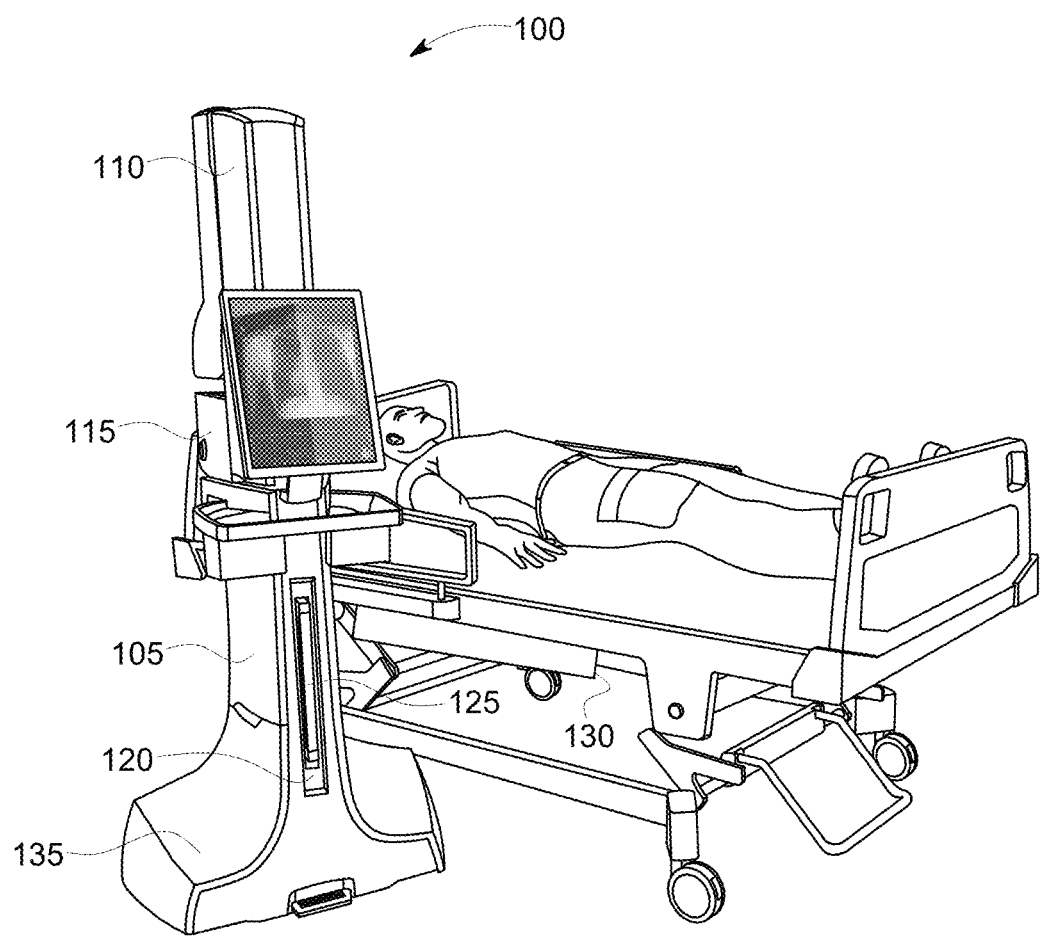
FIG. 1 shows an exemplary mobile X-ray system in a closed position according to the disclosed embodiments.

FIG. 1 shows an exemplary mobile X-ray system 100 according to the disclosed embodiments within a typical radiology suite. The term radiology suite generally refers to a room or rooms which are configured for performing radiology procedures typically using X-ray imaging techniques. Exemplary radiology procedures may include but are not limited to Computed Tomography (CT), computerized axial tomography (CAT) scanning, and fluoroscopy.

The disclosed embodiments are directed to a new type of mobile X-ray system that is compact and includes a movable base, a robotic arm mounted on the base, an X-ray source attached to the robotic arm, and a radiation detector. The base may have a relatively small footprint and a motorized drive system that may move the mobile X-ray system throughout the radiology suite and may also provide the base with the ability to rotate in place, that is, rotate around its vertical axis. The robotic arm may have multiple degrees of freedom provided by a number of robotic joints that may operate to move the robotic arm automatically or under manual control. The mobile X-ray system may also include a wireless connection between the mobile X-ray system and the detector. Dedicated sensors may detect the detector position in real time and the system may automatically move the base and the robotic arm to align the X-ray source with the detector. The mobile X-ray system may have one or more user interfaces to facilitate image acquisition.

Figure 2:
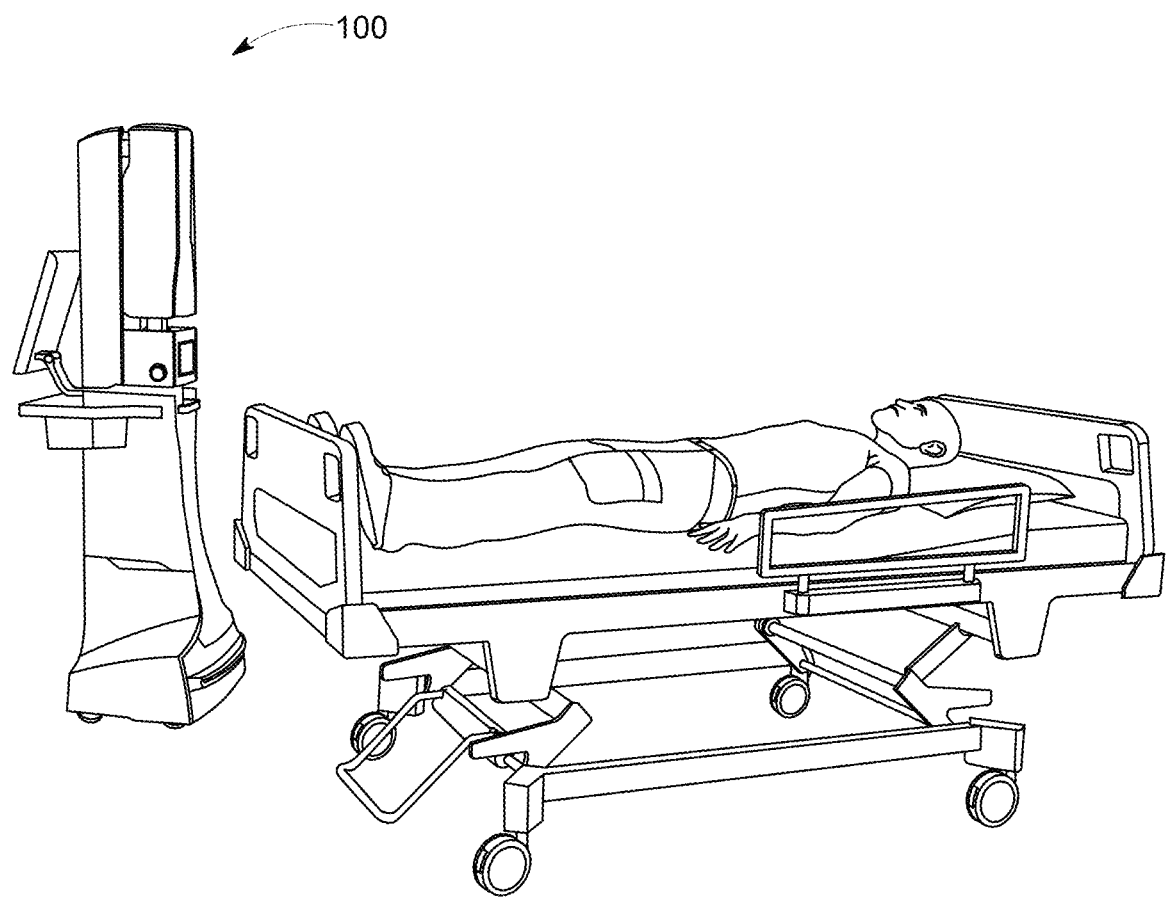
FIG. 2 shows a perspective view of the mobile X-ray system in a closed position.
Figure 3:
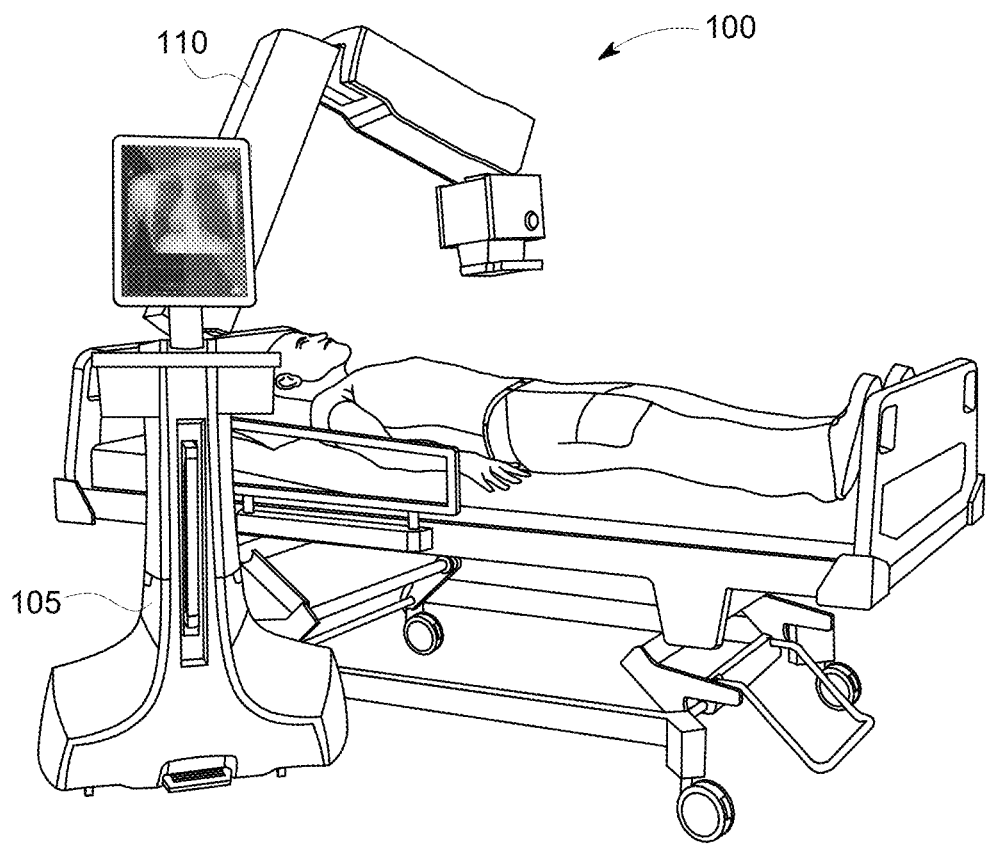
FIG. 3 shows a view of the mobile X-ray system in an open position.

As shown in FIG. 1, the exemplary mobile X-ray system 100 includes a base 105, a robotic arm 110 mounted to the base 105, and an X-ray source 115 attached to the robotic arm 110. A receptacle 120 may also be provided for storing and charging a detector 125. According to the disclosed embodiments, during scanning operations, the detector 125 may be positioned in a bucky 130 or other device for holding the detector 125 in close proximity to a patient. The mobile X-ray system includes covers 135 having surfaces without complex shapes that provide for easier cleaning. Cables of the mobile X-ray system 100 may be routed inside the covers 135 also providing for easier cleaning and a more sterile environment. FIG. 2 shows another perspective view of the mobile X-ray system 100 in a closed position. In the closed position, the mobile X-ray system 100 is compact, has a small footprint and occupies a small amount of space in the radiology suite. FIG. 3 shows a view of the mobile X-ray system 100 in an open position. The multiple degrees of freedom of the robotic arm 110 along with the movable base 105 provide an enhanced imaging capability.

Figure 4:
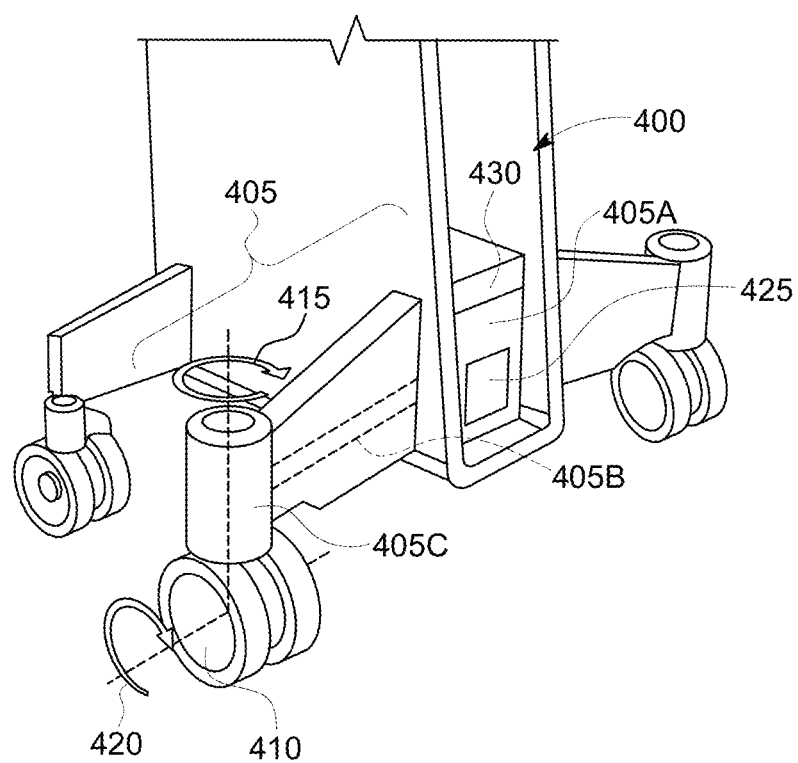
FIG. 4 shows a diagram of an exemplary drive system for the mobile X-ray system.

FIG. 4 shows a diagram of an exemplary drive system 400 for the mobile X-ray system 100. The drive system 400 may include a drive mechanism 405 and one or more drive wheels 410. In some embodiments, the drive mechanism 405 may include a motor 405A and a drive transmission unit 405B for providing power from the motor 405A to the drive wheel 410. The motor 405A may be powered by a portable power source 425, for example, a battery. The drive transmission unit 405B may include a drive shaft, drive belt, gearing, or any mechanism capable of driving the drive wheel 410 with steering forces in a horizontal plane shown by arrow 415 and motive forces in a vertical plane shown by arrow 420. In one exemplary embodiment a hub 405C may include gearing, one or more drive shafts or drive belts, or other mechanisms for converting the drive forces provided by drive transmission 405B to the steering and motive forces for drive wheel 410. In other embodiments, hub 405C may be driven directly by the portable power source 425 and may include any suitable driving mechanisms for providing steering and motive forces directly to drive wheel 410.

The mobile X-ray system 100 may include a controller 430 for controlling the overall operation of the mobile X-ray system 100, including controlling the drive system 400. The controller 430 may control an amount of power delivered by the portable power source 425, the operation of the motor 405A, the operation of the drive transmission unit 405B, the operations of the various embodiments of the hub 405C, and the operations of the drive wheel 410.

Figure 5:
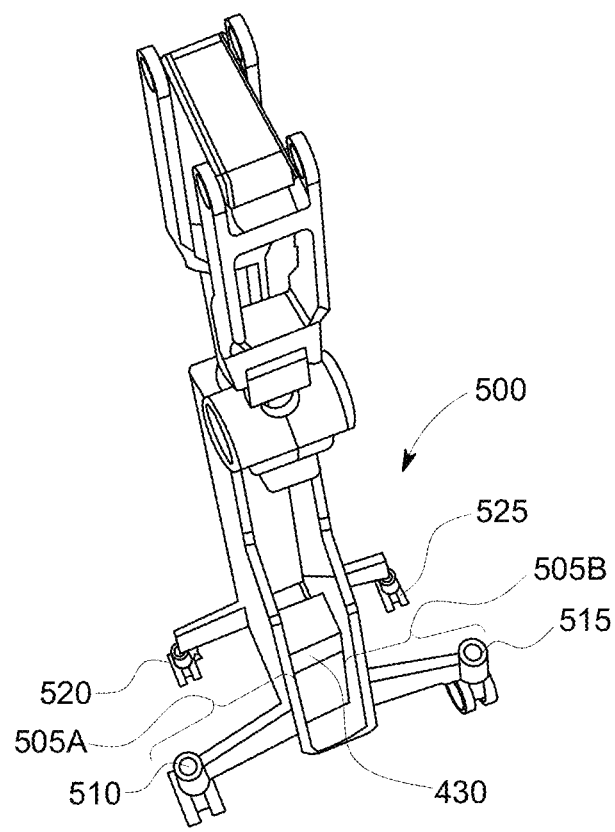
FIG. 5 shows an embodiment of the mobile X-ray system implemented with a drive system.

FIG. 5 shows an embodiment of the mobile X-ray system 100 implemented with a drive system 500 including two drive wheels 510, 515 and two wheels without any driving mechanism, referred to as free wheels, 520, 525. The drive system 500 for this embodiment may be substantially the same as drive system 400 and may include drive mechanisms 505A, 505B similar to drive mechanism 405, and may operate to drive the drive wheels 510, 515 individually and independently of each other. The controller 430 may operate to control the overall operation of the mobile X-ray system 100 including the drive system 500 and the operations of the drive wheels 505, 510.

While the disclosed embodiments are described as having one or two drive wheels, and in some aspects, two free wheels, it should be understood that the mobile X-ray system 100 may be configured with any suitable number of drive wheels and any suitable number of free wheels. It should also be understood that the controller 430 may cause the drive systems 400, 500 to move the mobile X-ray system 100 automatically or under manual control in any direction throughout the radiology suite. In some embodiments, the controller 430 may operate to automatically cause the base 105 and the robotic arm 110 to align the X-ray source 115 with the detector 125.

Figure 6:
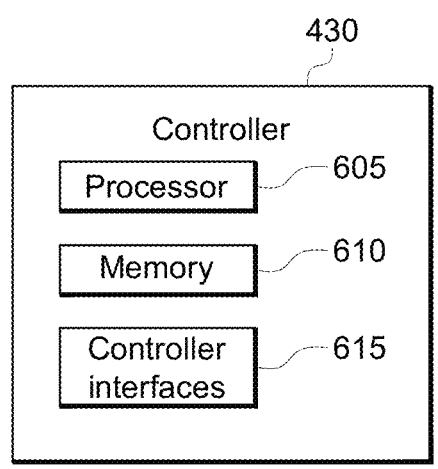
FIG. 6 depicts a block diagram of a controller of the mobile X-ray system.

FIG. 6 depicts a block diagram of the controller 430. The controller 430 may include a processor 605, a memory 610, and one or more controller interfaces 615. The controller 430 under control of programs in the memory 610 may control a frequency and amount of radiation produced by the X-ray source 115, the sensitivity of the detector 125, and the operation of the robotic arm 110. The one or more controller interfaces 615 may exchange signals and communications with the various components of the mobile X-ray system 100 and with other systems that may be remote from the mobile X-ray system 100. For example, the controller 430 may transmit image data to another remote system for review and analysis.

Figure 7A:
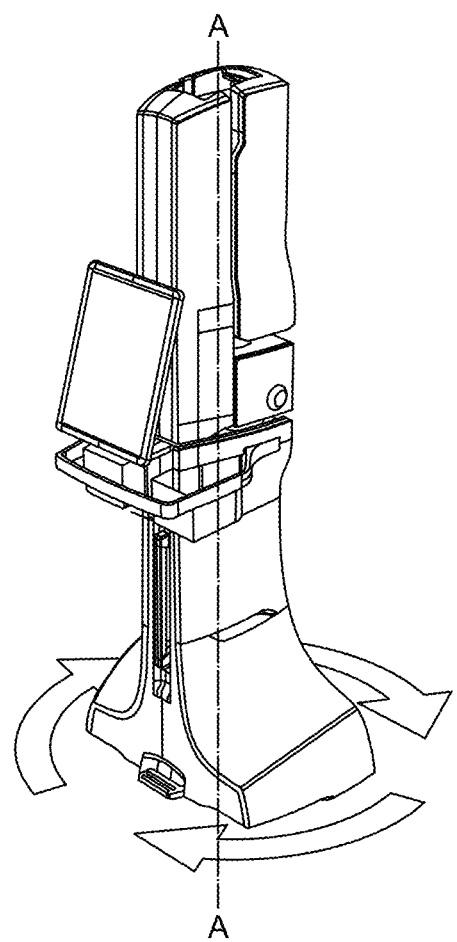
FIGS. 7A and 7B illustrate that the controller may control drive systems of the mobile X-ray system to rotate the mobile X-ray system in place.
Figure 7B:
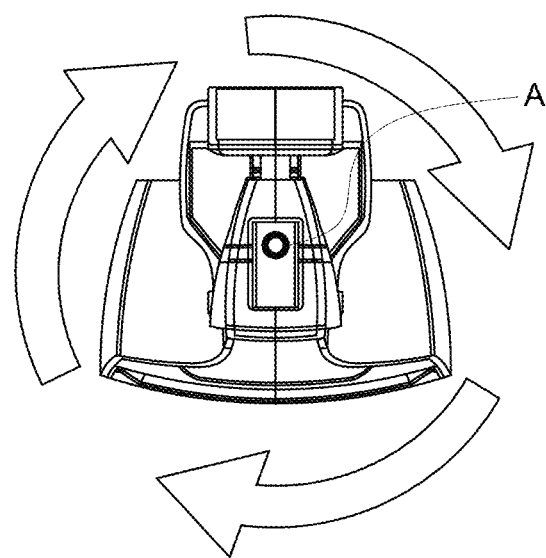

Referring to FIGS. 7A and 7B, in at least one aspect, the controller 430 may control the drive systems 400, 500 to provide the base 105 with the ability to rotate in place, that is, rotate around its vertical axis A. For example, the controller 430 may provide drive wheels 410, 510, 515 with steering forces in the horizontal plane shown by arrow 415 (FIG. 4) and motive forces in the vertical plane shown by arrow 420 (FIG. 4) to individually and independently align the drive wheels 410, 510, 515 and individually and independently drive them in directions that cause the mobile X-ray system 100 to rotate accordingly.

Figure 8:
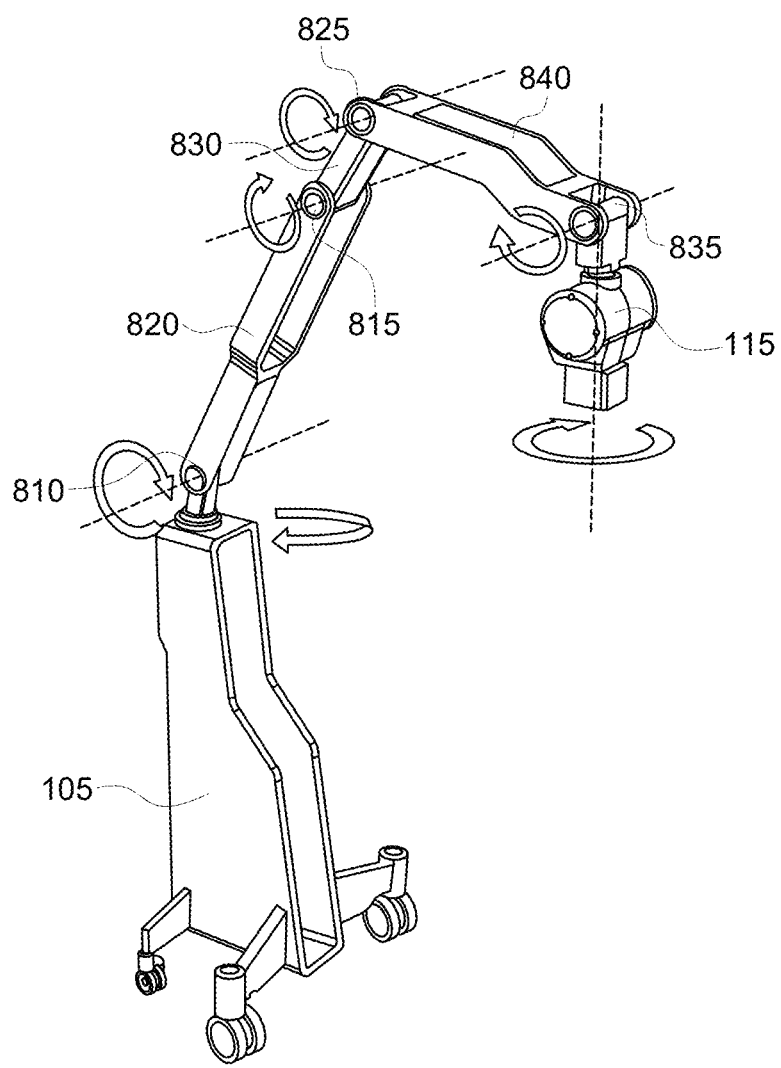
FIG. 8 shows a schematic diagram of a robotic arm and an X-ray source mounted on a base of the system.

FIG. 8 shows a schematic diagram of the robotic arm 110 and the X-ray source 115 mounted on the base 105. The robotic arm 110 may have a number of joints and linking components, for example, a waist joint 805 defining a first axis. The robotic arm 110 may also include a shoulder joint defining a second axis and a first elbow joint 815 defining a third axis. An upper arm member 820 may connect the shoulder joint 810 and the first elbow joint 815. The robotic arm 110 may also include a second elbow joint 825 defining a fourth axis and a mid-arm member 830 connecting the first and second elbow joints 815, 825. A wrist joint 835 defining a fifth axis may be connected to the second elbow joint 825 by a lower arm member 840. The wrist joint 835 may be coupled to the X-ray source 115. It should be understood that the various joints may have any suitable rotational capabilities or ranges. Each of the various joints may include one or more motors, sensors, or other robotic components, and may be controlled by controller 430 according to the disclosed embodiments.

While the robotic arm 110 is described as having five joints and three arm members, it should be understood that the robotic arm 110 may include any number of joints and any number of arm members suitable for positioning and orienting the X-ray source 115. The joints and arm members may operate under control of the controller 430 to automatically move the X-ray source 115 to any desired position at any desired speed. It should be understood that the base 105 and the robotic arm 110 may also be moved manually by an operator in a power assisted mode, and may include sensors, motors, and counterbalances at each joint and arm member that sense an application of external force and respond with movement in the force direction while the force is being applied. Each motor of the robotic arm 110 may have a torque control mode loop that operates to sense the external force and provide a responding force. Each drive wheel may also have sensors that work with the drive system 400, 500 to sense an applied force and provide a corresponding force in the applied force direction. Returning to FIG. 6A, the mobile X-ray system 100 may be equipped with an ergonomic handle to hold and manually move the robotic arm 110 or the entire mobile X-ray system 100.

Figure 9:
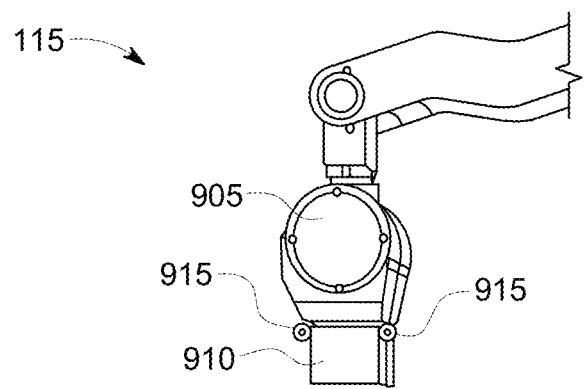
FIG. 9 shows an exemplary implementation of the X-ray source.

FIG. 9 shows an exemplary implementation of the X-ray source 115. The X-ray source 115 may include an X-ray generator 905, for example an X-ray tube, and a collimator 910. According to the disclosed embodiments, the X-ray source 115 may include one or more sensors 915 for determining a position and orientation of the detector 120.

Figure 10:
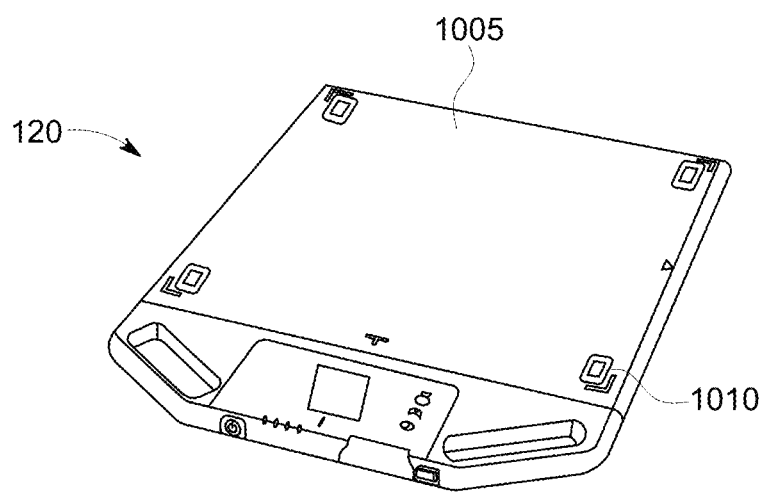
FIG. 10 shows an example of a detector of the mobile X-ray system.

FIG. 10 shows an example of the detector 120. The detector 120 may be a digital radiography receiver panel and may have a two dimensional detection plane 1005 for detecting X-rays. The detector 120 may communicate with the controller 430 and may provide image data from scanning procedures in real time. In some embodiments, the detector 120 may have a wireless communication capability and may be coupled wirelessly to the controller 430. In one or more embodiments, the detector 120 may store imaging data and output the imaging data when subsequently coupled to the controller 430. The detector 120 may also include one or more sensors 1010 that may communicate with the sensors 915 on the X-ray source 115.

The sensors 915 on the X-ray source 115 and the sensors 1010 on the detector 120 may be connected to the controller 430, for example, through one or more cables or through a wireless connection. The sensors 915, 1010 may provide signals or information to the controller 430, which in turn may operate the drive systems 400, 500 and the robotic arm 110 to automatically move the base 105 and the robotic arm 110 to align the X-ray source 115 with the detector 120 during scanning procedures. For example, the sensors 915 on the X-ray source may be distance sensors and the sensors 1010 on the detector 120 may be targets. In some embodiments, the sensors 915 may measure a distance from the sensors 915 to each of the sensors 1010 on the detector 120 and send the distance information to the controller 430. The controller 430 may calculate a position and orientation of the detector 120 with respect to the X-ray source 115 and then move one or more of the base 105 and the robotic arm 110 to achieve a particular alignment between the X-ray source 115 and the detector 120. In another example, the sensors 1010 on the detector 120 may be distance sensors and the sensors 915 on the X-ray source may be targets. The sensors 1010 on the detector may measure a distance to each of the sensors 915 on the X-ray source 115 and send the distance information to the controller 430. In still other embodiments, the sensors 915, 1010 are three dimensional position sensors and may each provide three dimensional position information to the controller 430. The controller 430 may use the three dimensional position information to calculate a position and orientation of the detector 120 with respect to the X-ray source 115 and then move one or more of the base 105 and the robotic arm 110 to achieve a particular alignment between the X-ray source 115 and the detector 120.

Figure 11:
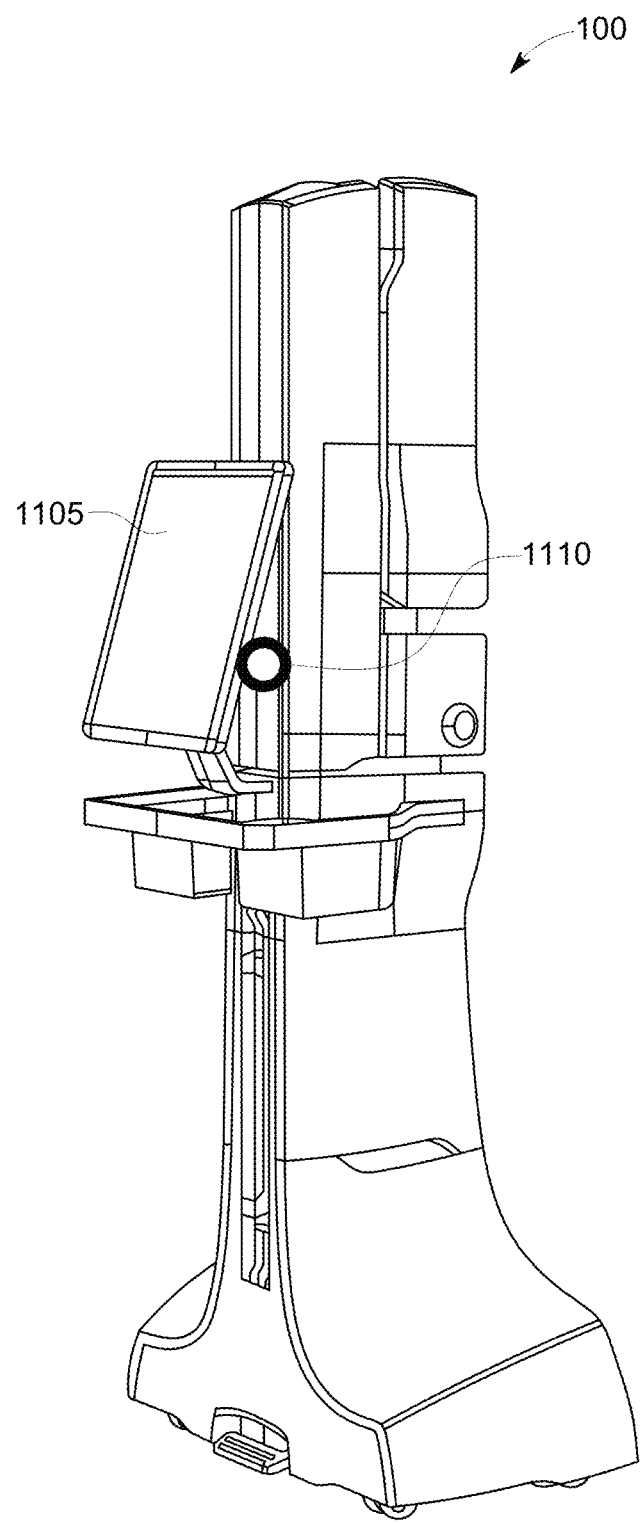
FIG. 11 shows a user interface of the mobile X-ray system in the form of a first display screen 1105.

Turning to FIG. 11, the mobile X-ray system 100 may include a number of user interfaces, including a first display screen 1105 mounted to the mobile X-ray system 100 that provides a user with the ability to control the mobile X-ray system 100. The first display screen 1105 may be implemented as a touch screen monitor or any other suitable interface that provides controls for the drive system 400, 500, the robotic arm 110, and the X-ray source 115. The first display screen 1105 may generally provide functions for moving the mobile X-ray system 100 and for controlling image acquisition, including moving the base 105 and the robotic arm 110 to achieve a particular alignment between the X-ray source 115 and the detector 120. The first display screen 1105 may also operate to display acquired images for viewing and analysis as they are collected or sometime after image acquisition. The first display screen 1105 may be attached to the mobile X-ray system 100 by a full motion mount 1110 that allows the first display screen to rotate and to be positioned in any desired orientation and position. In some embodiments, the detector 120 may transmit image data for review and analysis using the first display screen 1105.

Figure 12A:
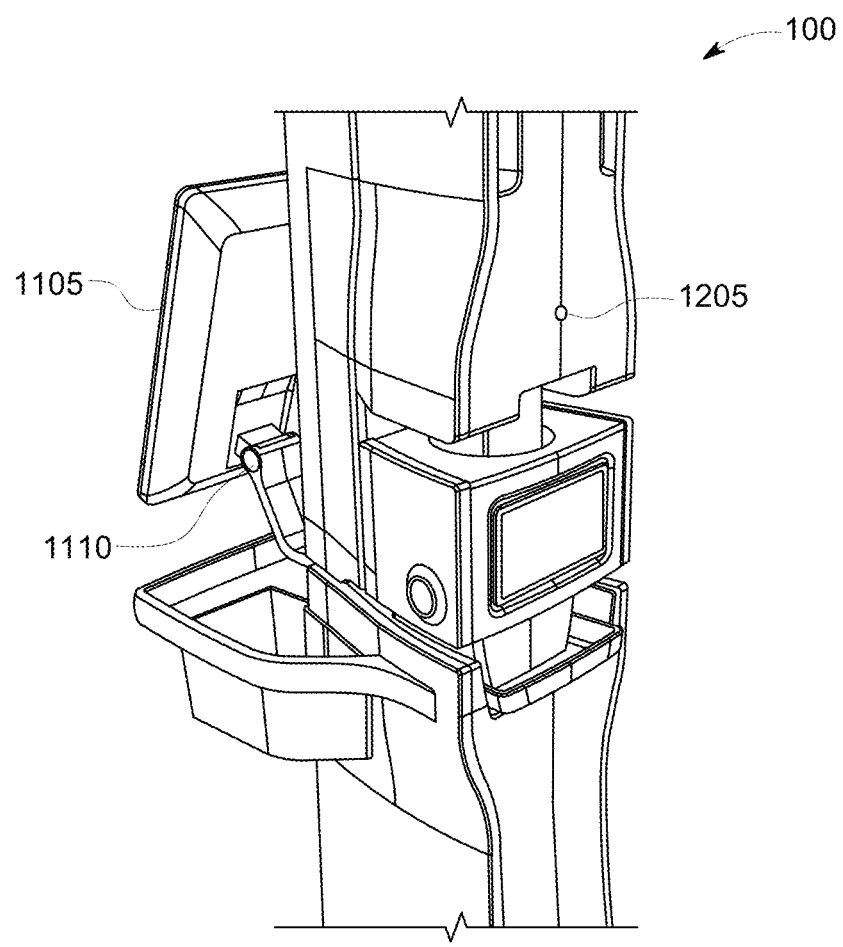
FIGS. 12A, 12B and 12C show an aspect of the operation of the first display screen and a camera.
Figure 12B:
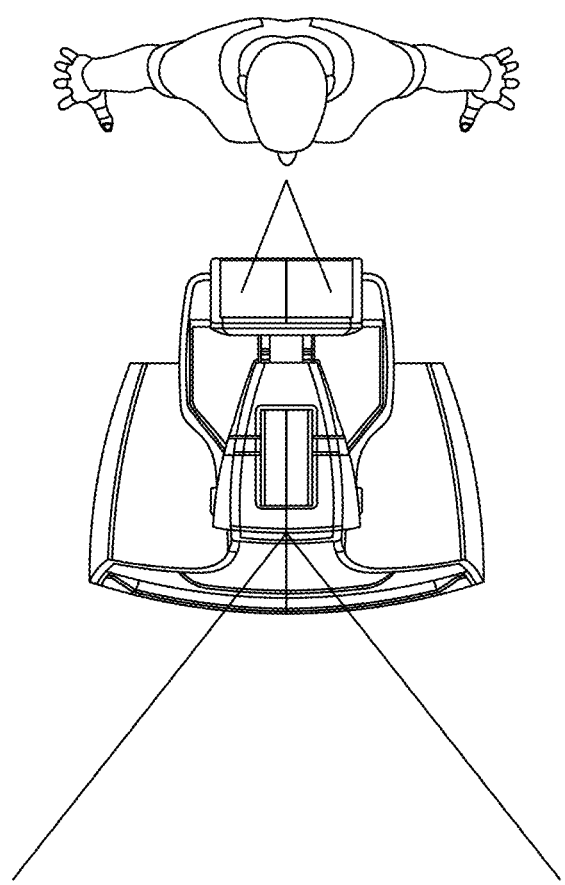
Figure 12C:
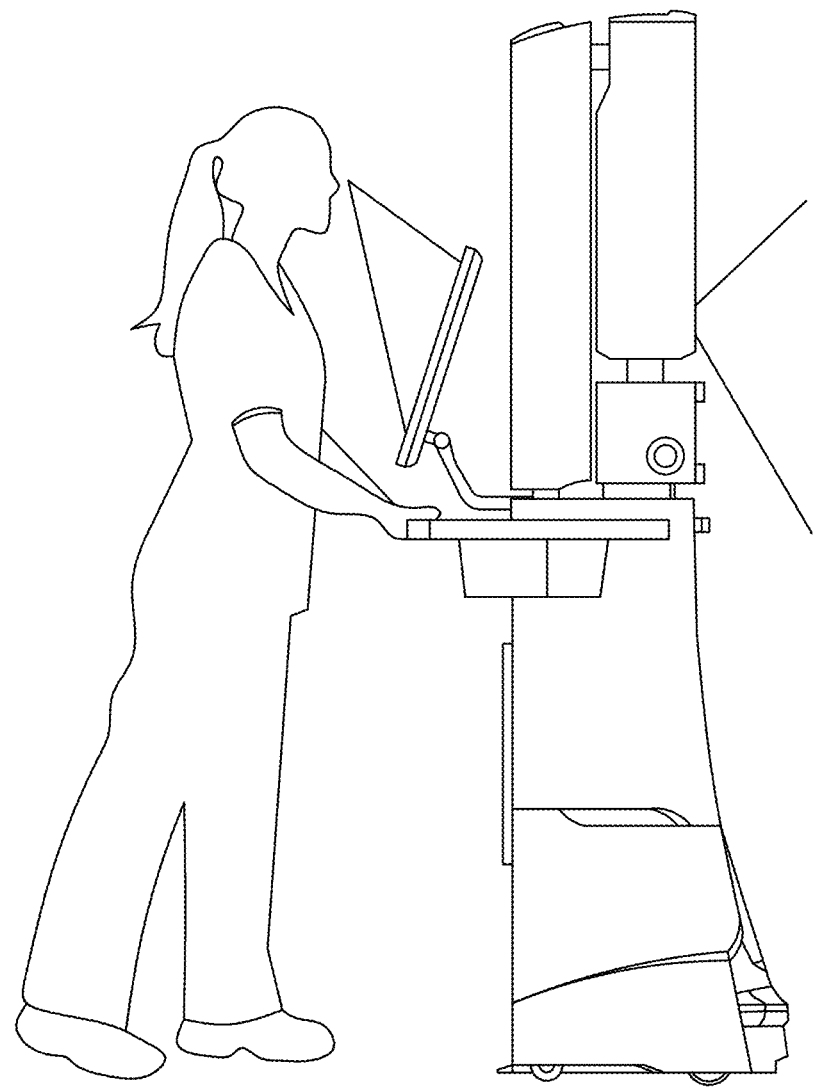

As shown in FIG. 12A, the mobile X-ray system 100 may include another user interface in the form of a camera 1205 attached to a side of the mobile X-ray system 100 opposite the first display screen 1105. Images collected by the camera 1205 may be transmitted to the first display screen 1105, and may provide a view of the area in front of the side of the mobile X-ray system 100 opposite the first display screen 1105. As shown in FIGS. 12B and 12C, the camera 1205 and first display screen 1105 provide a view that allows a user to see through to the opposite side of the mobile X-ray system 100, for example, to observe a patient or an area on that side of the mobile X-ray system.

Figure 13:
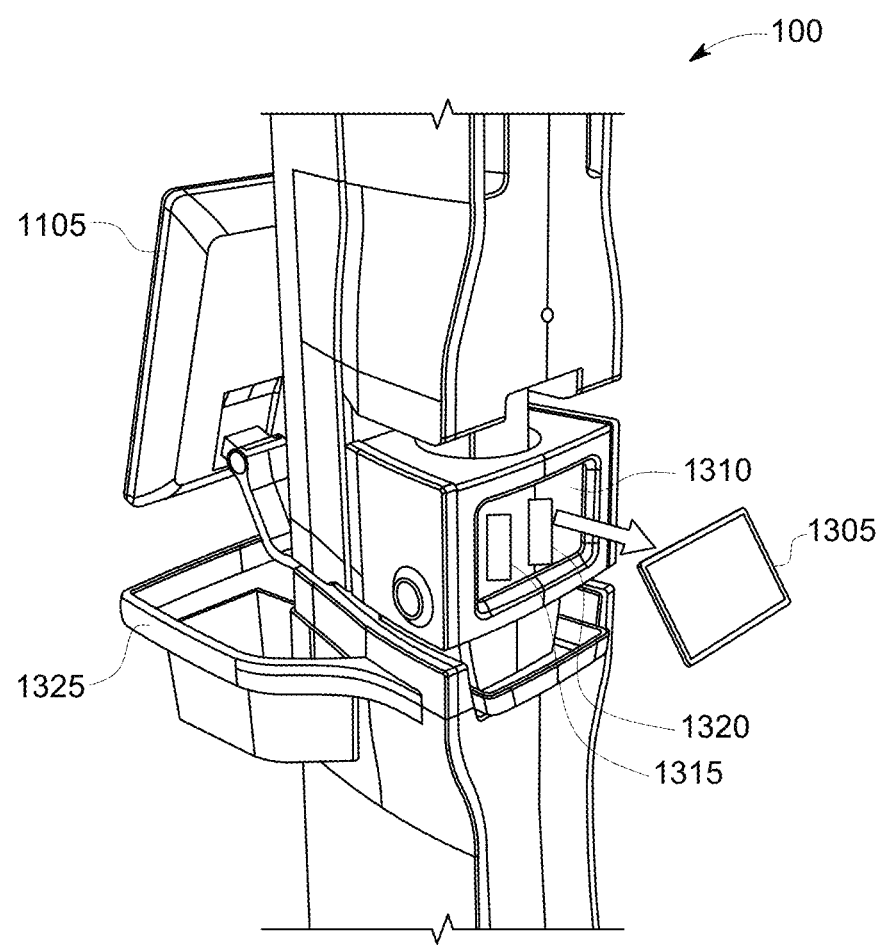
FIG. 13 shows a second display screen of the mobile X-ray system.

The mobile X-ray system 100 may have another user interface in the form of a second display screen 1305 mounted opposite the first display screen 1105, as shown in FIG. 13. The second display screen 1305 may be implemented as a detachable touch screen tablet. A receptacle 1310 in the mobile X-ray system 100 may be provided for the second display screen 1305, and may include a charging port 1315 to provide power to the second display screen 1305, and a data port 1320 for exchanging data between the second display screen 1305 and the controller 430. The second display screen 1305 may provide all the functionality of the first display screen 1105, including controlling the drive system 400, 500, the robotic arm 110, the X-ray source 115, providing functions for controlling movement of the mobile X-ray system 100, for controlling image acquisition, and for moving the base 105 and the robotic arm 110 to achieve a particular alignment between the X-ray source 115 and the detector 120. When detached from the mobile X-ray system 100, the second display screen 1305 may allow a user to operate the mobile X-ray system 100 remotely, providing an advantageous distance between the user and the X-ray source 115. In some embodiments, the mobile X-ray system 100 may also include a storage bin or facility 1325 to store supplies, for example, tape, pens, wipes, etc.

Figure 14:
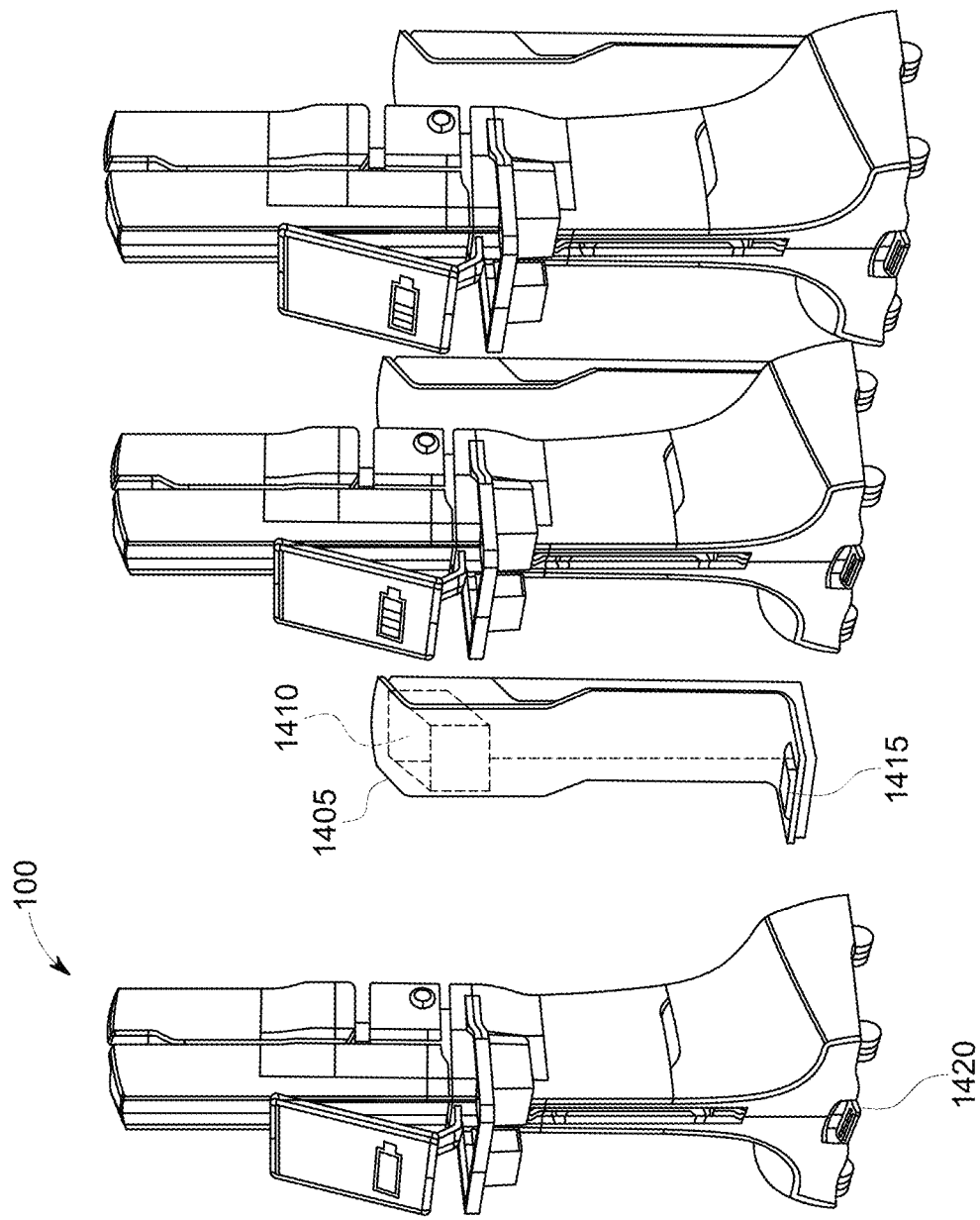
FIG. 14 shows one or more exemplary charging stations according to the disclosed embodiments.

The disclosed embodiments may also include one or more stations for charging the portable power source 425 of the mobile X-ray system 100. An exemplary charging station 1405 is shown in FIG. 14. The charging station 1405 may include a power source 1410 and a charging interface 1415 for contacting a corresponding interface 1420 in the mobile X-ray system 100. In some embodiments the charging interfaces 1415, 1420 may be wireless and may provide a non-contact charging capability.

The disclosed embodiments provide an enhanced mobile X-ray system 100 that provides a robotic arm 110 mounted on top of a base 105 in a vertical orientation, resulting in a sleek, less bulky system, that occupies relatively less floor space in the radiology suite. The motorized drive system 400, 500 provides the base 105 with the ability to rotate in place, that is, rotate around it's vertical axis, and also moves the base 105 as required to align the X-ray source 115 with the detector 125, resulting in an improved work flow. The enhanced freedom of movement of the base 105 and robotic arm 110 and the small footprint enable an adaptation to multiple types of room sizes and layouts, and makes the mobile X-ray system 100 easy to move to a patient location. The automated arm movement and multiple degrees of freedom provided by the robotic joints allows for positioning the X-ray source 115 in any position, for examining almost any region of interest from almost any angle. This flexibility is reinforced by the wireless connection between the mobile X-ray system 100 and the detector 125. The sensors 915 on the X-ray source 115 and detector 120 may detect the detector position in real time and in response, the robotic arm 110 and the base 105 may move automatically to align the X-ray source 115 with the detector 120.

In some aspects the mobile X-ray system disclosed herein may also contribute to a more relaxed patient environment. Preparation for examination or scanning procedures may be expedited because of the system's flexibility of movement. A user may position the detector and the robotic arm may adjust itself according to the detector position providing easier and faster X-ray source positioning.

Various modifications and adaptations may become apparent to those skilled in the relevant arts in view of the foregoing description, when read in conjunction with the accompanying drawings. However, all such and similar modifications of the teachings of the disclosed embodiments will still fall within the scope of the disclosed embodiments.

While the invention has been described with reference to exemplary embodiments, it will be understood by those skilled in the art that various changes may be made and equivalents may be substituted for elements thereof without departing from the scope of the invention. Furthermore, the skilled artisan will recognize the interchangeability of various features among different embodiments and that various aspects of different embodiments may be combined together. Similarly, the various method steps and features described, as well as other known equivalents for each such methods and feature, can be mixed and matched by one of ordinary skill in this art to construct additional assemblies and techniques in accordance with principles of this disclosure. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

Furthermore, some of the features of the exemplary embodiments could be used to advantage without the corresponding use of other features. As such, the foregoing description should be considered as merely illustrative of the principles of the disclosed embodiments and not in limitation thereof.

The invention claimed is:

1. A mobile X-ray system comprising:
 a movable base;
 a robotic arm mounted on the movable base;
 an X-ray source attached to the robotic arm;
 a radiation detector;
 one or more user interfaces; and
 a controller configured to determine a position of the X-ray source and a position of the detector and to automatically move both the base and the robotic arm to align the X-ray source with the detector.

2. The mobile X-ray system of claim 1, wherein the movable base comprises one or more drive wheels and a drive system configured to provide power to the one or more drive wheels.

3. The mobile X-ray system of claim 2, wherein the drive system is configured to provide steering forces in a horizontal plane and motive forces in a vertical plane to the one or more drive wheels.

4. The mobile X-ray system of claim 3, wherein the drive system is configured to provide the steering forces and motive forces to the one or more drive wheels to cause the mobile X-ray system to rotate around a vertical axis.

5. The mobile X-ray system of claim 1, wherein the robotic arm comprises a plurality of joints and arm members providing multiple degrees of freedom.

6. The mobile X-ray system of claim 1, comprising:
 one or more first sensors mounted on the X-ray source and one or more second sensors mounted on the detector, wherein the first and second sensors are connected to the controller, and the controller is configured to determine the position of the X-ray source and the detector from signals produced by the first and second sensors.

7. The mobile X-ray system of claim 6, wherein the first sensors are distance sensors configured to measure a distance to the second sensors and transmit the distance information to the controller, and wherein the controller is configured to determine the position of the X-ray source and the detector from the distance information.

8. The mobile X-ray system of claim 6, wherein the first and second sensors are three dimensional position sensors configured to transmit three dimensional position information to the controller, and wherein the controller is configured to determine the position of the X-ray source and the detector from the three dimensional position information.

9. The mobile X-ray system of claim 1, wherein the one or more user interfaces comprises a first display screen and a camera mounted on opposite sides of the mobile X-ray system, wherein images collected by the camera are transmitted to the first user interface to provide a view of an area in front of the mobile X-ray system opposite the first display screen.

10. The mobile X-ray system of claim 9, wherein the one or more user interfaces comprises a second detachable display screen for controlling movement and image acquisition of the mobile X-ray system.

11. A method of operating a mobile X-ray system comprising:
using a sensor system to determine a position of an X-ray source and a position of a radiation detector of the mobile X-ray system; and
using a controller to automatically move both a movable base and a robotic arm of the mobile X-ray system to align the X-ray source with the detector based on signals from the sensor system.

12. The method of claim 11, further comprising using the controller to operate a drive system of the mobile X-ray system to provide power to one or more drive wheels to move the movable base.

13. The method of claim 12 comprising using the controller to operate the drive system to provide steering forces in a horizontal plane and motive forces in a vertical plane to the one or more drive wheels to move the movable base.

14. The method of claim 13, comprising using the controller to operate the drive system to provide the steering forces and motive forces to the one or more drive wheels to cause the mobile X-ray system to rotate around a vertical axis.

15. The method of claim 11, wherein the sensor system comprises one or more first sensors mounted on the X-ray source and one or more second sensors mounted on the detector, the method comprising using the controller to determine the position of the X-ray source and the detector from signals produced by the first and second sensors.

16. The method of claim 15, comprising:
using the first sensors to measure a distance to the second sensors and transmit the distance information to the controller; and
using the controller to determine the position of the X-ray source and the detector from the distance information.

17. The method of claim 15, comprising:
using the first and second sensors to transmit three dimensional position information to the controller; and
using the controller to determine the position of the X-ray source and the detector from the three dimensional position information.

18. The method of claim 11, comprising using a first display screen and a camera mounted on opposite sides of the mobile X-ray system to provide a view of an area in front of the mobile X-ray system opposite the first display screen.

19. The method of claim 18, comprising using a second detachable display screen for controlling movement and image acquisition of the mobile X-ray system.

\* \* \* \* \*